US00PP33272P2

(12) United States Plant Patent
Ranney et al.

(10) Patent No.: US PP33,272 P2
(45) Date of Patent: Jul. 20, 2021

(54) ***BERBERIS* PLANT NAMED 'NCBT2'**

(50) Latin Name: *Berberis thunbergii*
Varietal Denomination: NCBT2

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/902,848

(22) Filed: Jun. 16, 2020

(51) Int. Cl.
*A01H 5/12* (2018.01)
*A01H 6/00* (2018.01)

(52) U.S. Cl.
USPC ..... Plt./241

(58) Field of Classification Search
USPC ..... Plt./241, 226
CPC ... A01H 5/12; A01H 5/08; A01H 5/02; A01H 5/00; A01H 6/00
See application file for complete search history.

(56) References Cited

PUBLICATIONS

Wright Proven Winners ColorChoice Shrubs 2020 introductions from Spring Meadow Nursery, retrieved on Nov. 16, 2020, retrieved from the Internet at https://www.greenhousegrower.com/crops/ornamentals/proven-winners-colorchoice-2020-introductions-from-spring-meadow-nursery/#Tinsel/149422/1, 3 pp. (Year: 2020).*
Proven winners Sunjoy Neo Barberry, retrieved on Nov. 16, 2020, retrieved from the Internet at https://www.provenwinners.com/plants/berberis/sunjoy-neo-barberry-berberis-thunbergii, 5 pp. (Year: 2020).*

* cited by examiner

*Primary Examiner* — June Hwu
(74) *Attorney, Agent, or Firm* — Cassandra Bright

(57) ABSTRACT

A new and distinct cultivar of *Berberis* plant named 'NCBT2' is disclosed, characterized by a semi-compact rounded habit, reddish orange to moderate red spring foliage, deep red to vivid red exterior summer foliage and yellow green interior foliage. The new variety is a *Berberis*, normally produced as an outdoor garden or container plant.

3 Drawing Sheets

Latin name of the genus and species: *Berberis thunbergii*.
Variety denomination: 'NCBT2'.

BACKGROUND OF THE INVENTION

The new *Berberis* cultivar is a product of a planned breeding program conducted by the inventors in Mills River, N.C. The cross resulting in this new variety was made during Spring of 2006.

'NCBT2' is a hybrid between *Berberis thunbergii* 'Golden Devine', NCSU 2007-035 (unpatented, female parent) and *Berberis thunbergii* 'Thornless', NCSU 1999-181 (unpatented, male parent). The new variety was identified as a potentially interesting selection in the Summer of 2007, at a research greenhouse in Mills River, N.C.

The first asexual propagation of 'NCBT2' was carried out in June 2008 by rooting stem cuttings at the same research greenhouse in Mills River, N.C. and has been asexually reproduced repeatedly by vegetative cuttings over a 12-year period. 'NCBT2' roots readily from softwood cuttings treated with a basal dip of 4,000-5,000 ppm indole butyric acid (potassium salt) in water. 'NCBT2' has been found to retain its distinctive characteristics through successive asexual propagations.

SUMMARY OF THE INVENTION

The cultivar 'NCBT2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCBT2' These characteristics in combination distinguish 'NCBT2' as a new and distinct *Berberis* cultivar:

1. Reddish orange to moderate red spring foliage, deep red to vivid red exterior summer foliage and yellow green interior foliage.
2. Semi-compact, rounded habit.

PARENT COMPARISON

Plants of the new cultivar 'NCBT2' are similar to plants of the seed parent in most horticultural characteristics, however, plants of the new cultivar 'NCBT2' differ in the following;

1. The new variety has red-orange foliage. The seed parent has yellow-green foliage.

Plants of the new cultivar 'NCBT2' are similar to plants of the pollen parent in most horticultural characteristics, however, plants of the new cultivar 'NCBT2' differ in the following;

1. The new variety produces an average amount of thorns. The pollen parent has few to no thorns.

COMMERCIAL COMPARISON

Plants of the new cultivar 'NCBT2' can be compared to the commercial variety *Berberis* 'O'Byrne' U.S. Plant Pat.

No. 26,546. These varieties are similar in most horticultural characteristics; however 'NCBT2' differs in the following:

1. 'NCBT2' has Greyed-Purple (185A), (187B), or Vivid Red (46C) mature leaves (upper surface) while 'O'Byrne' has mature leaves that are Vivid Reddish Orange (34A) with Yellow-Green (154B) margins.
2. Plants of the new variety produce lateral branches approximately perpendicular to main branch to angled slightly upwards distally, this comparator branches outward in an arching form.

BRIEF DESCRIPTION OF THE PHOTOGRAPHS

This new *Berberis* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Berberis*.

DETAILED BOTANICAL DESCRIPTION

Figure 1:
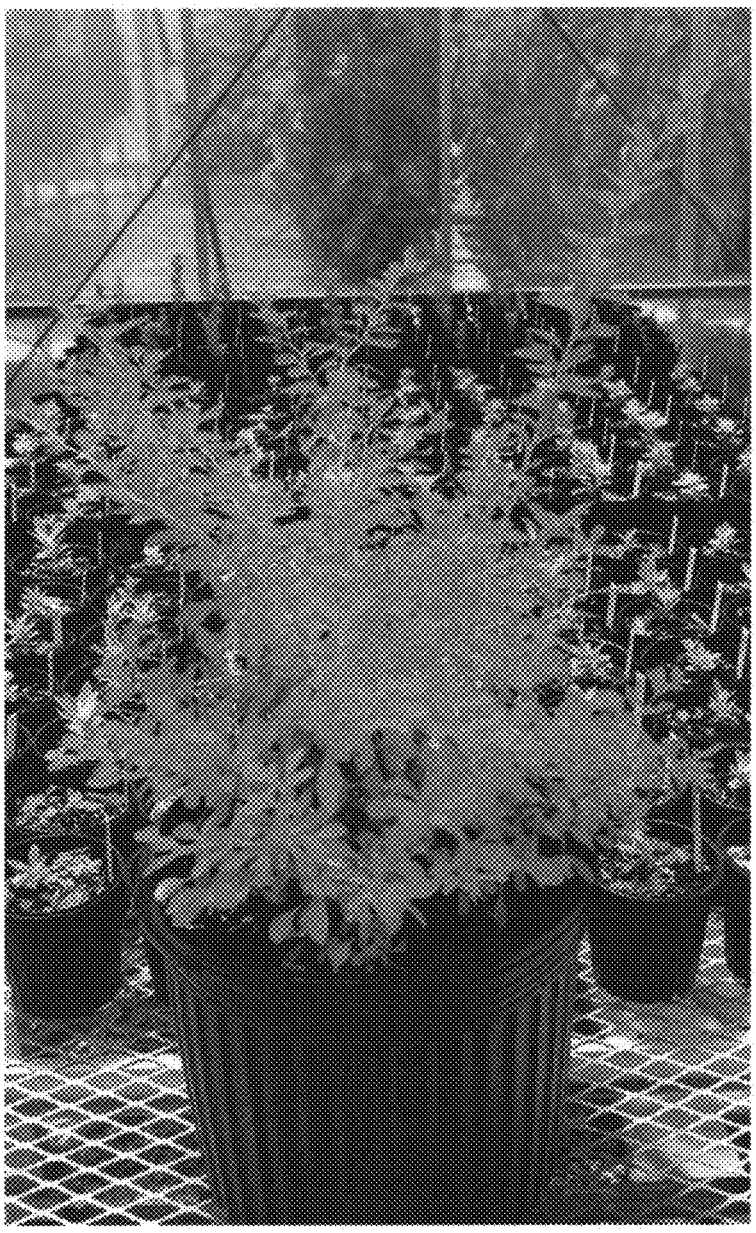
FIG. 1 is a color photograph of 'NCBT2' showing the form and foliage of a 2-year-old container-grown plant taken in Mills River, N.C. in June 2010.
Figure 2:
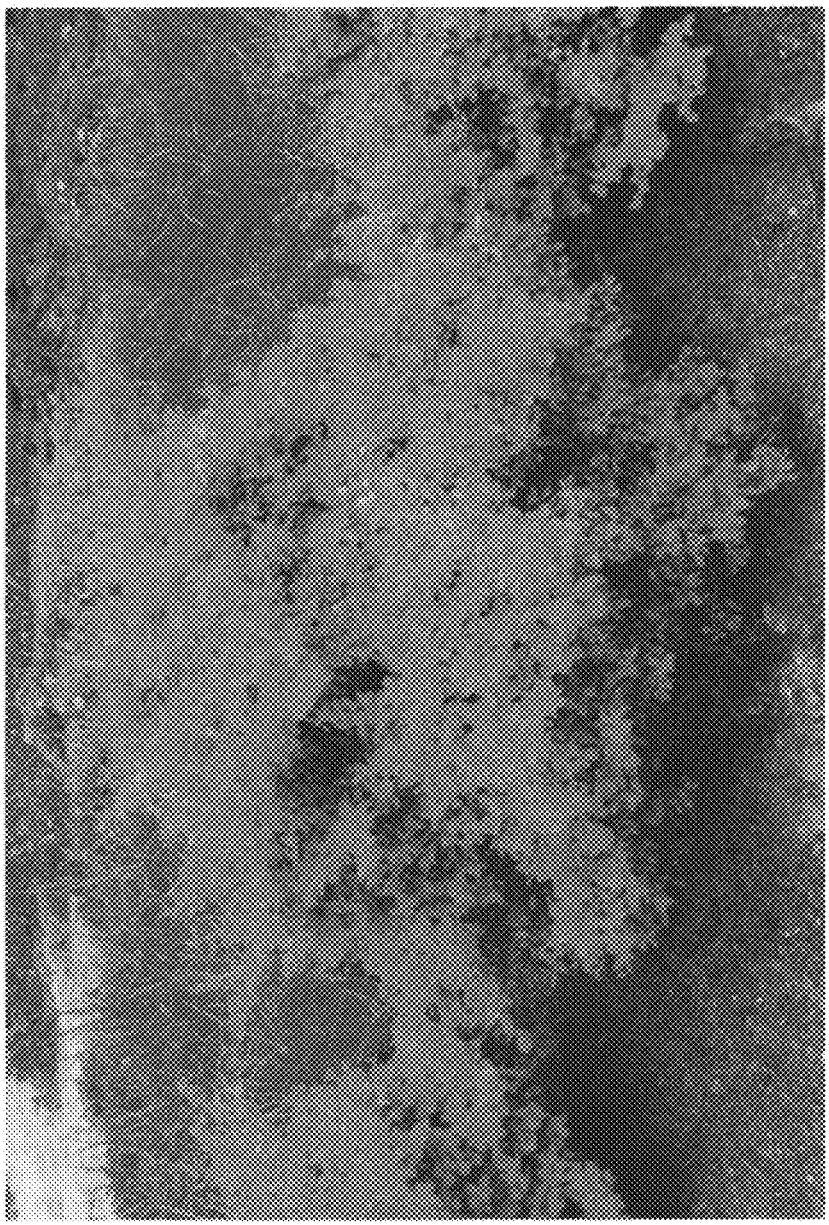
FIG. 2 is a color photograph of 'NCBT2' showing the form and foliage of a 5-year-old field-grown plant taken in Mills River, N.C. in July 2017.
Figure 3:
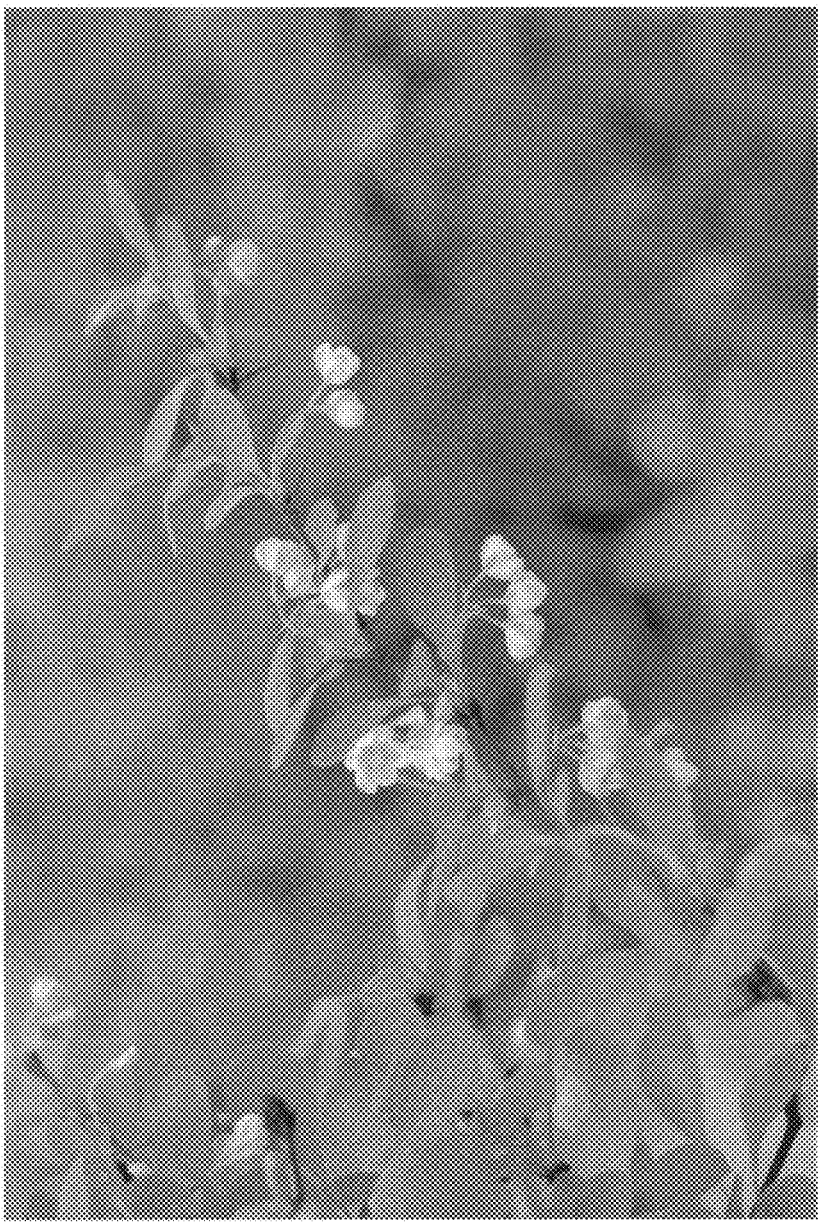
FIG. 3 is a color photograph showing the flowers and spring foliage of a 3-year-old container-grown plant of 'NCBT2' taken in Mills River, N.C. in April 2020.

The following is a detailed description of the botanical characteristics of the new and distinct *Berberis* variety plant known by the denomination 'NCBT2'. The detailed description was taken on a three-year-old (2019) and four-year-old (2020) container-grown plant in Mills River, N.C. All colors cited herein refer to The Royal Horticultural Society Colour Chart (The Royal Horticultural Society (R.H.S.), London, Sixth Edition (2015). Where specific dimensions, sizes, colors, and other characteristics are given, it is to be understood that such characteristics are approximations or averages set forth as accurately as practicable.

Botanical classification: *Berberis thunbergii* 'NCBT2'.

PROPAGATION

Time to initiate roots: About 20 days at approximately 18 to 27° C.

Root description: Density is moderate to dense, fibrous, freely branching. Mature root is colored Yellow 9B.

Time to produce a rooted young plant: About 90 days.

PLANT

Plant type: Perennial deciduous shrub.

Growth habit: Semi-compact, rounded.

Overall plant shape: Upright/rounded.

Height: 60 to 90 cm 4 year old plant.

Plant spread: 70 to 95 cm 4 year old plant.

Growth rate: Moderate.

Plant vigor: Good.

Shoot and stem:

*Branching characteristics*.—Alternate whorled

*Lateral branch length*.—Avg. 22 cm (10 to 40 cm).

*Lateral branch aspect*.—Approximately perpendicular to main branch to angled slightly upward distally.

*Lateral branch quantity*.—Between 4 and 10 per 10 cm.

*Lateral branch diameter*.—Avg. 2.6 mm (1.2 to 4.1 mm).

*Internode length*.—Avg. 11 mm (8.0 to 15 mm).

*Lateral branch texture* (*current year*).—Glabrous.

*Lateral branch color* (*current year*).—Near Greyed-Red 180A.

*Lateral branch color* (*previous year*).—Near Greyed-Orange 175B.

*Lateral branch color* (*mature*).—Near Grey-Brown N199B.

*Immature shoot color* (*current year*).—Near Red N45A.

*Maturing stem color* (*current year*).—Near Yellow-Green 151A flecked with Red N45A.

*Mature stem color*.—Near Brown 200A.

*Mature stem texture*.—Glabrous.

FOLIAGE

Leaf:

*Arrangement*.—Alternate whorled, single

*Shape*.—Spatulate, occasionally rhombic.

*Apex*.—Acute, occasionally mucronate with less than 1 mm spike.

*Base*.—Attenuate.

*Venation*.—Pinnate.

*Surface appearance*.—Both upper and lower surfaces matte.

*Surface texture*.—Both and upper and lower surfaces glabrous.

*Margins*.—Entire.

*Length* (*fully expanded*).—Avg. 26 mm (17.6 to 32.9 mm).

*Width* (*fully expanded*).—Avg. 11.8 mm (6.4 to 14.1 mm).

*Exterior emerging leaves*.—Color: Upper surface: Some leaves near Greyed-Red 179A, others near Greyed-Red 178C. Lower surface: Near Greyed-Red 182C to 182D. Upper vein color: Near Yellow-Green 145A or Yellow-Green N144A. Lower vein color: Similar to lamina color, closest to Greyed-Red 182C. Texture: Glabrous.

*Interior emerging leaves*.—Color: Upper surface: Near Yellow-Green 145A or Yellow-Green N144A. Lower surface: Near Yellow-Green 151A. Upper vein color: Near Yellow-Green 145A or Yellow-Green N144A. Lower vein color: Near Yellow-Green 151A. Texture: Glabrous.

*Exterior mature leaves during growing season*.—Color: Upper surface: Some leaves near Greyed-Purple 185A, others near Greyed-Purple 187B or Vivid Red 46C. Lower surface: Some leaves near Greyed-Red 182B, others near Greyed-Green 195B. Upper vein color: Some veins near Orange-Red N34A, others Yellow-Green N144B. Lower vein color: Similar to lower surface color with some veins Greyed-Purple 185A and others Greyed-Green 195B. Texture: Glabrous.

*Interior mature leaves during growing season*.—Color: Upper surface: Near Yellow-Green N144C. Lower surface: Near Yellow-Green 145B. Upper vein color:

Similar to upper surface color, near Yellow-Green N144C. Lower vein color: Similar to lower surface color, near Yellow-Green 145B. Texture: Glabrous.

*Exterior mature leaves during fall season*.—Color: Upper surface: Some leaves near Red 53A, others near Red 46A and others Red N45B ranging to Red N45C. Lower surface: Some leaves near Grey-Brown 199D, others Greyed-Red 180C and others Greyed-Purple 185D. Upper vein color: Some veins near Red 53A, others near Green-Yellow 151C. Lower vein color: Near Red N45C. Texture: Glabrous.

*Interior mature leaves during fall season*.—Color: Upper surface: Near Yellow-Green N144C. Lower surface: Near Yellow-Green N144D. Upper vein color: Near Yellow-Green N144C. Lower vein color: Near Yellow-Green N144C. Texture: Glabrous.

*Petiole*.—Color: Upper surface: Same as leaf lamina. Lower surface: Same as leaf lamina. Length: Avg. 7.5 mm (3.0 to 13.9 mm). Diameter: Avg. 0.4 mm (0.16 to 0.79 mm). Texture: Glabrous.

*Foliage durability*.—Foliage very durable to stress.

*Spines/thorns*.—Attached to plant nodes, occurring 1 or 3 spines at each node. Length: Avg. 6.9 mm (5.9 to 9.0 mm). Width at base: Avg. 0.4 mm (0.2 to 0.7 mm). Width at tip: Avg. 0.1 mm (0.1 to 0.2 mm). Color: Immature: Near Yellow-Green N144A and occasionally Yellow 12C. Mature: Near Grey-Brown N199B. Previous year: Near Greyed-Orange 175B. Texture: Glabrous.

FLOWER

Inflorescence:

*Description*.—Umbellate fascicles, sometimes solitary.

*Number of flowers per inflorescence*.—1 to 4.

*Flowering season*.—Spring.

*Flower longevity on plant*.—2 weeks, self-cleaning.

*Fragrance*.—Typical *Berberis thunbergii* fragrance, slightly aromatic.

*Inflorescence*.—Diameter: Avg. 9.6 mm (7.8 to 11.0 mm). Length: Avg. 10.0 mm (8.8 to 13.6 mm).

*Flower*.—Diameter: Avg. 8.7 mm (7.6 to 9.5 mm). Height: Avg. 4.1 mm (3.6 to 4.6 mm).

*Bud*.—Shape: Globose. Length: Avg. 3.6 mm (3.1 to 4.0 mm). Width: Avg. 3.1 mm (2.6 to 3.5 mm). Color: The sepal midsection is near Red 46B with sepal margins near Yellow 5B imparting a "beach ball pattern" of alternating red, yellow and red to the bud.

*Petals*.—Number and arrangement: One whorl of 5 to 6. Length: Avg. 3.8 mm (3.3 to 4.5 mm). Width: Avg. 2.3 mm (1.8 to 2.6 mm). Shape: Ovate, occasionally with truncate apex. Margin: Entire. Base: Truncate. Texture: Glabrous. Color: Upper surface: Near Yellow 7D. Lower surface: Near Yellow 7D.

*Sepal*.—Number and arrangement: Two whorls of 3. Length: Avg. 3 mm (2.5 to 4.3 mm). Width: Avg. 1.2 mm (0.6 to 2.5 mm). Shape: Ovate with acute and occasionally obtuse apex. Margin: Entire. Base: Truncate. Texture: Glabrous. Color: Upper surface: Mostly near Red 45B when up to balloon stage. At balloon stage to anthesis near Red 45B in center with margin near Yellow 7D. Lower surface: Mostly Red 47B when up to balloon stage. At balloon stage to anthesis Red 47D center with margins Yellow 5D.

*Peduncle*.—Length: Avg. 4.7 mm (3.5 to 5.7 mm). Diameter: Avg. 0.4 mm (0.3 to 0.5 mm). Texture: Glabrous. Color: Near Red 46B.

*Pedicels*.—Length: Avg. 3.4 mm (2.8 to 3.9 mm). Diameter: Avg. 0.28 mm (0.21 to 0.36 mm). Texture: Glabrous. Color: Near Red 46B.

*Bracts*.—2 to 3 per inflorescence, insignificant in size and not accurately measured.

REPRODUCTIVE ORGANS

Gynoecium:

*Pistil number*.—1.

*Pistil length*.—Avg. 2.5 mm (2.1 to 3.1 mm).

*Stigma shape*.—Flattened globose with central depression.

*Stigma diameter*.—Avg. 1.2 mm (1.2 to 1.4 mm).

*Stigma color*.—Near Yellow 12A.

*Ovary length*.—Avg. 2.0 mm (2.0 to 2.5 mm).

*Ovary color*.—Near Yellow 6).

*Style length*.—Avg. 3.0 mm (1.7 to 3.6 mm).

*Style color*.—Near Yellow 7C.

Androecium:

*Stamen number*.—5 or 6.

*Filament length*.—Avg. 2.5 mm (2 to 3 mm).

*Filament color*.—Near Yellow 7C.

*Anther shape*.—Two lobed.

*Anther size*.—Avg. 0.2 mm (0.2 to 0.3 mm).

*Anther color*.—Near Yellow 5B.

*Amount of pollen*.—Scant.

*Pollen color*.—Near Yellow 4B.

OTHER CHARACTERISTICS

Seeds and fruits: Not observed to date.

Disease/pest resistance: 'NCBT2' is documented to be resistant to Wheat Rust (*Puccinia* sp.). Neither resistance nor susceptibility to other diseases and pests of *Berberis* have been observed.

Temperature tolerance: Cold tolerance to least USDA zone 6B; with potential to zone 4 based upon parentage but testing has not been completed in colder zones. Upper temperature range tolerance unknown.

What is claimed is:

1. A new and distinct cultivar of *Berberis* plant named 'NCBT2' as herein illustrated and described.

* * * * *